(12) United States Patent
Fischer, Jr.

(10) Patent No.: US 10,617,508 B2
(45) Date of Patent: Apr. 14, 2020

(54) VENA CAVA FILTER WITH DUAL RETRIEVAL

(71) Applicant: COOK MEDICAL TECHNOLOGIES LLC, Bloomington, IN (US)

(72) Inventor: Frank J. Fischer, Jr., Bloomington, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 346 days.

(21) Appl. No.: 15/804,351

(22) Filed: Nov. 6, 2017

(65) Prior Publication Data

US 2018/0055618 A1  Mar. 1, 2018

Related U.S. Application Data

(62) Division of application No. 13/611,821, filed on Sep. 12, 2012, now Pat. No. 9,833,305.

(51) Int. Cl.
*A61F 2/01* (2006.01)

(52) U.S. Cl.
CPC .......... *A61F 2/01* (2013.01); *A61F 2002/011* (2013.01); *A61F 2002/016* (2013.01); *A61F 2230/005* (2013.01); *A61F 2230/0078* (2013.01)

(58) Field of Classification Search
CPC .................. A61F 2/01; A61F 2002/011; A61F 2002/016; A61F 2230/005; A61F 2230/0078
See application file for complete search history.

(56) References Cited

U.S. PATENT DOCUMENTS 4,619,246 A  10/1986  Molgaard-Nielsen et al.
5,324,304 A  6/1994  Rasmussen
(Continued)

FOREIGN PATENT DOCUMENTS

JP   2003/508115 A   3/2003
WO   WO 2001/015630 A1   3/2001
WO   WO 2007/143602 A2   12/2007

OTHER PUBLICATIONS

Communication for EP Application No. 13179309.3-1651 dated Dec. 7, 2015.
(Continued)

*Primary Examiner* — Tan-Uyen T Ho
*Assistant Examiner* — Rachel S Highland
(74) *Attorney, Agent, or Firm* — Brinks Gilson & Lione

(57) ABSTRACT

An intravascular filter assembly has an expanded state for capturing thrombi in a patient's blood vessel, a first a collapsed state for removal from the patient's blood vessel in a first direction and a second collapsed state for removal from the patient's blood vessel in a second direction. A plurality of first struts extends from a first axial side of a fixed hub, and a plurality of second struts extends from the opposite axial side of the fixed hub. An axially movable hub has a first position radially surrounding the tubular body, a second position axially spaced apart from the fixed hub along the first struts, and a third position axially spaced apart from the fixed hub along the second struts. The first struts are collapsed when the movable hub is in the second position, and the second struts are collapsed when the movable hub is in the third position.

4 Claims, 4 Drawing Sheets

(56) References Cited

U.S. PATENT DOCUMENTS

| | | |
|---|---|---|
| 5,370,657 A | 12/1994 | Irie |
| 6,306,163 B1 | 10/2001 | Fitz |
| 6,447,530 B1 | 9/2002 | Ostrovsky et al. |
| 6,872,217 B2 | 3/2005 | Walak et al. |
| 7,033,376 B2 | 4/2006 | Tsukernik |
| 7,857,826 B2 | 12/2010 | Eskuri et al. |
| 8,029,529 B1 | 10/2011 | Chanduszko |
| 2005/0131451 A1 | 6/2005 | Kleshinski et al. |
| 2005/0159771 A1 | 7/2005 | Petersen |
| 2005/0267514 A1 | 12/2005 | Osborne et al. |
| 2010/0016882 A1 | 1/2010 | Lapid |
| 2010/0160954 A1 | 6/2010 | Osborne |
| 2011/0125180 A1 | 5/2011 | Tripp et al. |
| 2013/0103073 A1* | 4/2013 | Honeycutt ............... A61F 2/01 606/200 |

OTHER PUBLICATIONS

Japanese Application No. 2013-168598, Office Action dated Feb. 14, 2017.

* cited by examiner

VENA CAVA FILTER WITH DUAL RETRIEVAL

CROSS-REFERENCE TO RELATED APPLICATIONS

The present application is a Divisional from U.S. patent application Ser. No. 13/611,821, filed Sep. 12, 2012, the foregoing application is hereby incorporated by reference in its entirety.

BACKGROUND OF THE INVENTION

The present invention relates to medical devices. More particularly, the invention relates to a removable vena cava clot filter that can be percutaneously placed in and removed from the vena cava of a patient.

A need for filtering devices arises in trauma patients, orthopedic surgery patients, neurosurgery patients, or in patients having medical conditions requiring bed rest or non-movement. During such medical conditions, filtering devices are inserted to prevent thromboses in the peripheral vasculature of patients when thrombi break away from the vessel wall, risking downstream embolism or embolization. For example, depending on the size, such thrombi pose a serious risk of pulmonary embolism wherein blood clots migrate from the peripheral vasculature through the heart and into the lungs.

The benefits of a vena cava filter have been well established. After deployment of a filter in a patient, proliferating intimal cells begin to accumulate around filter struts that contact the wall of the vessel. After a length of time, such ingrowth poses difficulties for removal of the filter. In addition, typical filter deployment and retrieval are directionally dependent. For example, filters inserted using a femoral approach may require the retrieval to take place through a jugular approach. A vena cava filter that can be easily retrieved independent of the orientation of the filter deployment within the vessel

SUMMARY OF THE INVENTION

According to one aspect of the invention, an intravascular filter assembly has an expanded state for capturing thrombi in a patient's blood vessel, a first a collapsed state for removal from the patient's blood vessel in a first direction and a second collapsed state for removal from the patient's blood vessel in a second direction. The filter assembly comprises a fixed hub defining a tubular body; a plurality of first struts extending from a first axial side of the fixed hub, the first struts having an expanded configuration when the filter is in the expanded state and a collapsed configuration when the filter is in the first collapsed state; a plurality of second struts extending from a second axial side of the fixed hub opposite the first axial side of the fixed hub, the second struts having an expanded configuration when the filter is in the expanded state and a collapsed configuration when the filter is in the second collapsed state; an axially movable hub having a first position radially surrounding at least an axial portion of the tubular body, a second position axially spaced apart from the fixed hub along the first struts, and a third position axially spaced apart from the fixed hub along the second struts, the first struts being in the collapsed configuration when the movable hub is in the second position, and the second struts being in the collapsed configuration when the movable hub is in the third position; a first coupling member extending from a first axial side of the movable hub, the first axial side of the movable hub coinciding with the first axial side of the fixed hub; and a second coupling member extending from a second axial side of the movable hub opposite the first axial side of the movable hub. Thus, one movable hub is sufficient to create either one of the two collapsed states.

According to another aspect of the invention, the fixed hub may have an axial passage formed therethrough. Such an axial passage allows access to the interior of the filter assembly through the fixed hub.

According to a further aspect of the invention, an elongated push tool with a tip having a diameter greater than the axial passage and smaller than a distance of opposing struts adjacent the fixed hub may be used for holding the fixed hub in an axial location while the movable hub is moved relative to the fixed hub.

According to another aspect of the invention, at least one of the first and second coupling members may form a retainer limiting a distance of travel of the movable hub along the struts, thus performing a dual function.

According to another aspect of the invention, one retainer may be formed by a first hook forming the first coupling member. For example, the first hook may have an axial length determining the third position of the movable hub.

In a similar manner, the second retainer may be formed by a second hook forming the second coupling member. The second hook may have an axial length determining the second position of the movable hub.

According to yet another aspect of the invention, each of the struts may have a first curved portion bending the strut away from a longitudinal axis of the filter and a second curved portion bending the strut toward the longitudinal axis of the filter. For first struts of this shape, the second position of the movable hub is preferably at least as far away from the fixed hub as the first curved portion of each of the first struts strut. Likewise, for second struts of this shape, the third position of the movable hub is preferably at least as far away from the fixed up as the first curved portion of each of the second struts.

According to a further aspect of the invention, the filter assembly has two substantially identical axial halves arranged on opposite axial sides of a virtual radial plane centrally intersecting the fixed hub. This arrangement provides equal functions on both axial sides and thus allows deployment of the filter assembly without regard to the axial orientation. There is no wrong orientation of arranging the filter assembly in a delivery catheter or sheath and no wrong direction of deployment.

According to another aspect of the present invention, where the filter assembly has the filter assembly having a fixed hub defining a tubular body; a plurality of first struts extending from a first axial side of the fixed hub, the first struts having an expanded configuration when the filter is in an expanded state and a collapsed configuration when the filter is in a first collapsed state; a plurality of second struts extending from a second axial side of the fixed hub opposite the first axial side of the fixed hub, the second struts having an expanded configuration when the filter is in the expanded state and a collapsed configuration when the filter is in a second collapsed state; an axially movable hub having a first position radially surrounding at least an axial portion of the tubular body, a second position axially spaced apart from the fixed hub along the first struts, and a third position axially spaced apart from the fixed hub along the second struts, the first struts being in the collapsed configuration when the movable hub is in the second position, and the second struts being in the collapsed configuration when the movable hub is in the third position; a first coupling member extending from a first axial side of the movable hub, the first axial side of the movable hub coinciding with the first axial side of the fixed hub; and a second coupling member extending from a second axial side of the movable hub opposite the first axial side of the movable hub; a method of removing an intravascular filter assembly from a body vessel comprises the steps of inserting a recovery sheath with a lumen into the body vessel from the first axial side; placing a recovery tool within the lumen of the recovery sheath and moving it distally toward the filter assembly; engaging the first coupling member with the recovery tool; placing a push tool within the lumen of the recovery sheath and moving it distally toward the filter assembly; abutting and retaining the fixed hub at a fixed location; pulling the movable hub off the tubular portion along the struts until the movable hub is in the second position and the struts are in the collapsed configuration; proximally removing the push tool; causing a relative movement between the filter assembly and the recovery sheath in a direction that causes the filter assembly to enter the lumen of the recovery sheath; collapsing the second struts with the recovery sheath by a further relative movement between the filter assembly and the recovery sheath; continuing the relative movement between the filter assembly and the recovery sheath until the entire filter assembly is surrounded by the recovery sheath; and proximally removing the recovery sheath including the filter assembly. Accordingly, only the set of struts arranged on the proximal side of the filter assembly need to be collapsed for entry into the recover sheath. The distal set of struts is collapsed automatically by the recovery sheath via the relative movement between the filter assembly and the recovery sheath. This can be accomplished by either moving the recovery sheath distally or by pulling the filter assembly proximally.

The push tool and the recovery sheath may be removed simultaneously or consecutively.

According to another aspect of the invention, if the filter assembly further includes a retainer limiting a movement of the movable hub along the struts and thereby defining the second position of the movable hub, the movable hub is moved until the retainer limits the movement.

According to another aspect of the invention, the retainer may be a hook with a dual function that limits the movement of the movable hub by abutting the fixed hub.

Further aspects, features, and advantages of the invention will become apparent from consideration of the following description and the appended claims when taken in connection with the accompanying drawings.

DETAILED DESCRIPTION OF THE DRAWINGS

The following drawings are included for illustrative purposes only and are not intended to limit the scope of the present invention. The drawings are of a purely schematic nature and are not drawn to scale. In particular, any elongated elements such as struts and wires are shown shortened in FIGS. 2 and 3.

Figure 1:
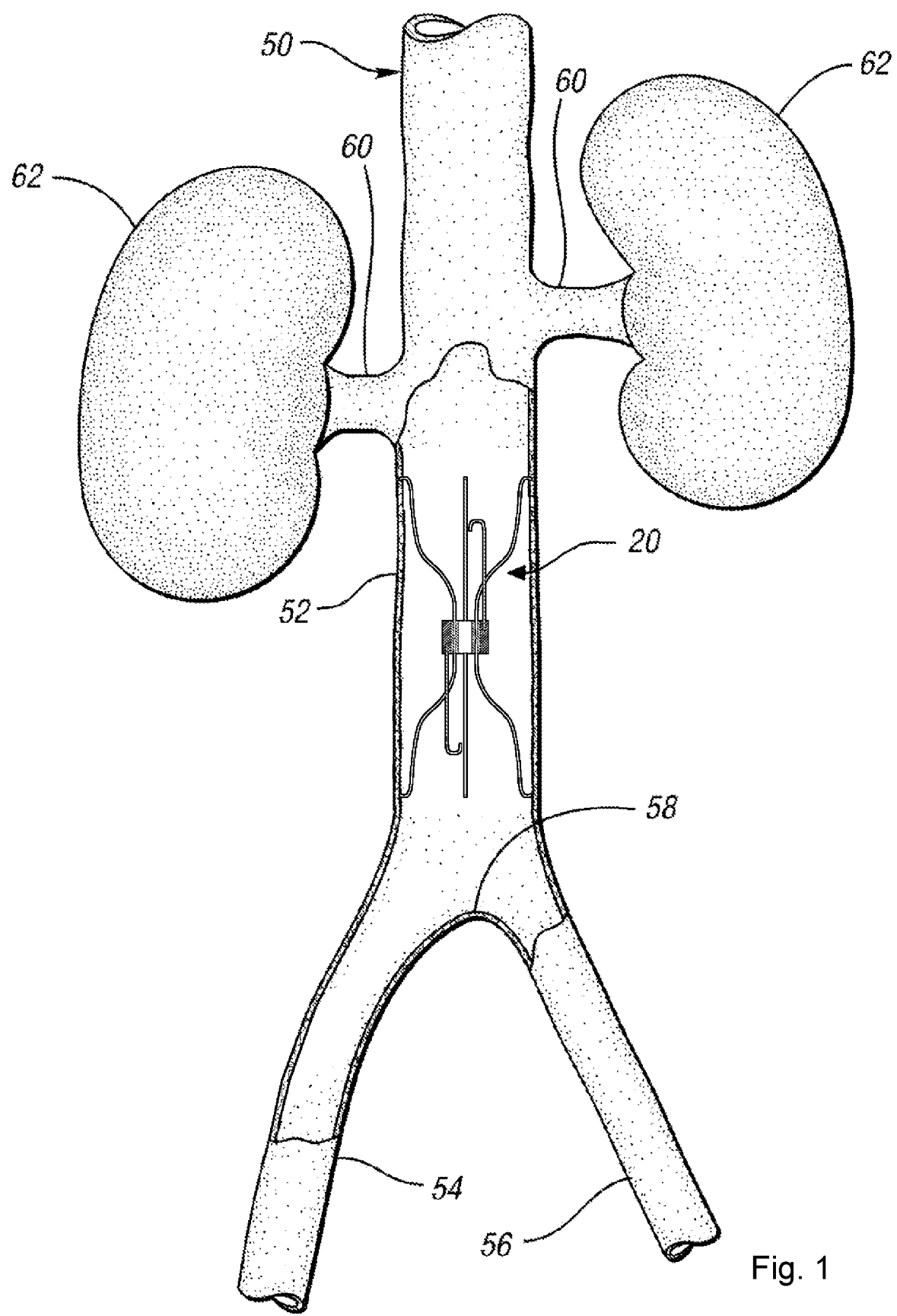
FIG. 1 is an illustration of the anatomy of the renal veins, the femoral veins, and the vena cava, in which one embodiment of a vena cava filter of the present invention is deployed.

In accordance with a first embodiment of the present invention, FIG. 1 illustrates a vena cava filter 20 implanted in a vena cava 50 for the purpose of lysing or capturing thrombi carried by the blood flowing through the femoral veins 54 and 56 toward the heart and into the pulmonary arteries. As shown, the femoral veins 54 and 56 from the legs merge at juncture 58 into the vena cava 50. The renal veins 60 from the kidneys 62 join the vena cava 50 downstream of juncture 58. The portion of the vena cava 50, between the juncture 58 and the renal veins 60, defines the inferior vena cava 52 in which the vena cava filter 20 has been percutaneously deployed through one of the femoral veins 54. Preferably, the vena cava filter 20 has a length smaller than the length of the inferior vena cava 52. Because a typical inferior vena cava has a length between about 8 cm and about 13 cm, the filter 20 may have a length between about 5 cm and about 10 cm, for example about 6 cm to about 8 cm. The length of a filter 20 for deployment in an individual patient may be selected based on the individual patient's anatomy.

Figure 2:
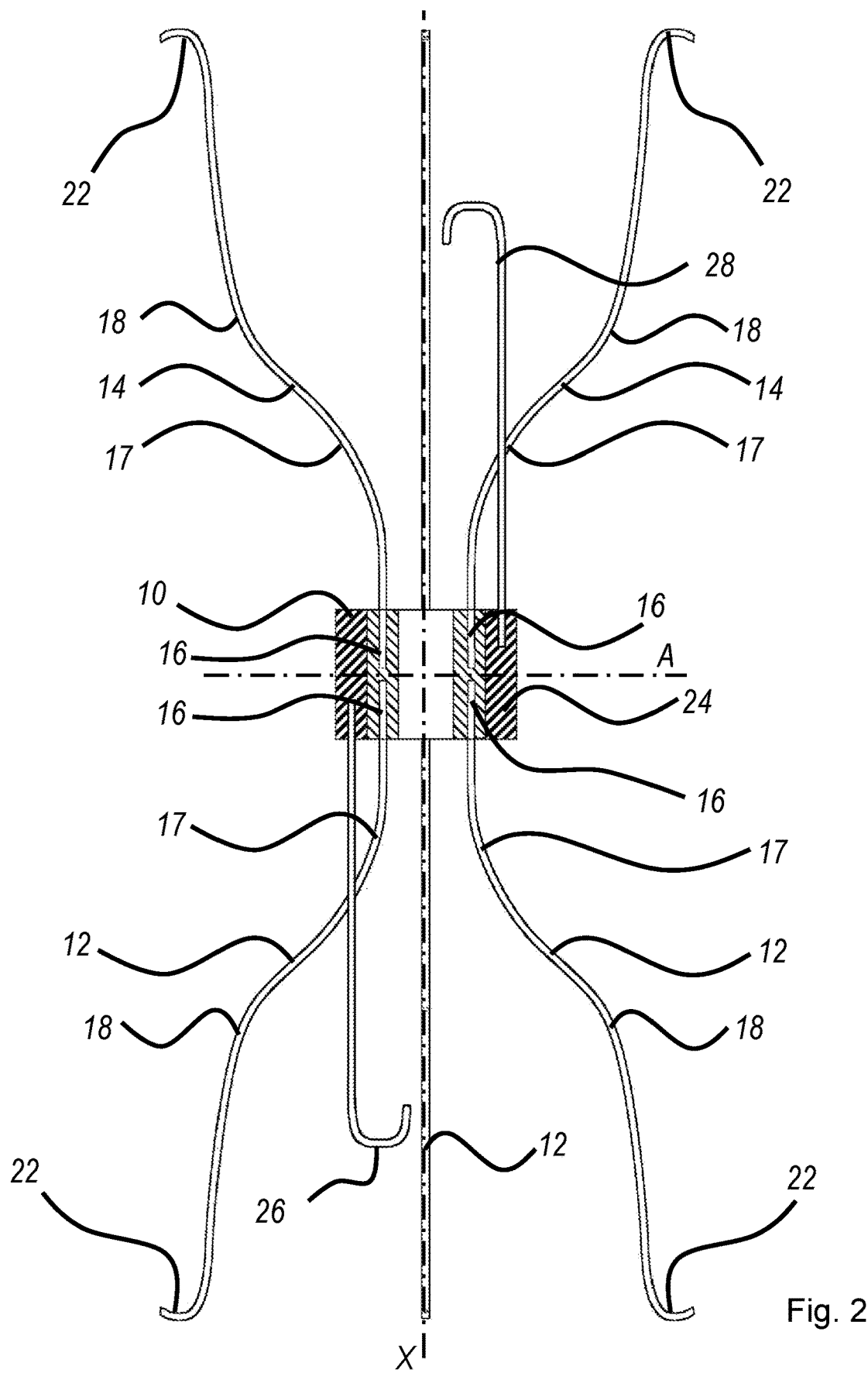
FIG. 2 is a cross-sectional view of one embodiment of the vena cava filter of the present invention in an expanded configuration.

One embodiment of the present invention will be discussed with reference to FIGS. 2 and 3 in which filter 20 is shown. FIG. 2 illustrates a cross-section of filter 20 in an expanded configuration. The filter 20 comprises a fixed hub 10 with eight struts 12 and 14, in two axially opposed sets of four femoral struts 12 and four jugular struts 14. The femoral struts 12 of the first set each have fixed ends 16 that are secured in the fixed hub 10. Likewise, the jugular struts 14 of the second set axially opposed the first set of struts 12 have fixed ends 16 secured in the fixed hub 10. In the cross-sectional view of FIG. 2, only three of the four struts 12 and 14 of each set are visible. Any other number of struts per set, such as two, three, five, or six, is also within the scope of the invention. While a greater number of struts may be suited to filter thrombi of a smaller size, they also occupy a larger diameter of the fixed hub 10. Thus an optimum number of struts 12 and 14 may depend on the specific patient and application. The fixed hub 10 acts to prevent twisting or crossing of struts 12 and 14 during implantation and recovery procedures. Fixed hub 10 secures the fixed ends 16 of struts 12 and 14 together in a compact bundle to define a central or longitudinal axis X of the filter. The fixed hub 10 has a minimal diameter for the size of wire used to form the struts 12 and 14.

Preferably, the struts 12 and 14 are formed from stainless steel wire, MP35N, Nitinol, or any other suitable superelastic material that will result in a self-opening or self-expanding filter. In this embodiment, the struts 12 are formed from wire having a round cross-section with a diameter of about 0.015 inches. Of course, it is not necessary that the struts 12 and 14 have a round cross-section. For example, the struts 12 and 14 could have a square shaped or other suitable shaped cross section without falling beyond the scope or spirit of the present invention. The fixed hub may be formed from steel or any other biocompatible metal or from a suitable plastic material.

Each strut 12 and 14 is formed with a first curved portion 17 that is configured to bend away from the longitudinal or central axis X of the filter 20 and a second curved portion 18 that is configured to bend toward the longitudinal axis of the filter 20. Each strut 12 maintains a non-parallel relationship with the longitudinal axis X of the filter 20. Opposite the fixed ends 16, the struts 12 and 14 terminate at anchoring hooks 22 that will anchor in the vessel wall when the filter 20 is deployed at a delivery location in the blood vessel. When the filter 20 is deployed, the anchoring hooks 22 define two radial planes in which the filter 20 is secured in the blood vessel. The anchoring hooks 22 prevent the filter 20 from migrating from the delivery location in the blood vessel where it has been deposited. The struts 12 and 14 are shaped and dimensioned such that, when the filter 20 is deployed and expanded, the filter 20 has a diameter of about 35 mm and a length of about 10 cm. For example, when expanded, the filter 20 may have a diameter of between about 30 mm and 40 mm, and a length of between about 3 cm and 7 cm. The struts 12 have sufficient spring strength that when the filter is deployed, the anchoring hooks 22 will securely engage the vessel wall.

The fixed hub 10 maintains the struts 12 in their preset configuration with respect to one another. In the shown embodiment, the fixed hub 10 forms a tubular body. The term "tubular body" is used in the broad sense of having a generally cylindrical shape. Alternatively, the tubular body of the fixed hub 10 may be solid without a central lumen.

A sleeve-shaped movable hub 24 surrounds the fixed hub 10. The movable hub 24 is dimensioned to have a close fit around the fixed hub 10 so that it does not slip off the fixed hub 10 absent an external pulling force. The movable hub may be made of the same material as the fixed hub or a different biocompatible material that does not exhibit a chemical reaction with any other material used.

Secured on the movable hub 24 are a femoral hook 26 and a jugular hook 28. The femoral hook 26 extends to the axial side of the struts 12 and is configured to engage with a snare introduced through the femoral vein for femoral retrieval of filter 20, as will be explained in greater detail in connection with FIG. 3. The jugular hook 28 extends to the axial side of the struts 14 and is configured to engage with a snare introduced through the jugular vein for jugular retrieval of the filter 20. Both the femoral hook 26 and the jugular hook 28 are dimensioned to limit an axial distance that the movable hub 24 is intended to travel along the struts 12 and 14, respectively.

The shown embodiments, the filter 20 has two identical axial halves arranged on two axial sides of a virtual radial plane A centrally intersecting the fixed hub 10. In FIG. 2, these identical halves are arranged circumferentially offset by 180 degrees. But as will be explained in connection with FIG. 4, they may also form mirror images of each other with respect to the radial plane A. By having similar struts extend from both axial sides of the fixed hub 10 with anchoring hooks 22 at both axial ends of the filter 20, the filter 20 ensures a proper radially centered and axially aligned position after deployment.

It is, however, within the scope of the invention to provide for an asymmetrical arrangement, in which, for example, one set of struts 12 may have a different length than the other set of struts 14. Likewise, the femoral and jugular coupling members, such as femoral hook 26 and jugular hook 28 may have different lengths. Where the length of struts 12 differs from the length of struts 14, the jugular hook 28 may be adapted to the length of the femoral hooks 12, and the femoral hook may be adapted to the jugular hooks 14.

The delivery process and the jugular retrieval process are generally known in the art. For deployment of the filter 20, a delivery tube (not shown) is percutaneously inserted through the patient's vessels such that the distal end of the delivery tube is at the location of deployment. For example, a wire guide (not shown) can be used to guide the delivery tube to the location of deployment. The filter is preferably inserted through the proximal end of the delivery tube with the jugular hook 28 leading and the struts 12 trailing. During delivery, the struts 12 are optionally collapsed by moving the movable hub 24 along the struts 12 until the jugular hook 28 abuts the collar 18. For a more complete disclosure of a filter delivery system that may be used to deliver the filter 20 to a desired location, reference may be made to U.S. Pat. No. 5,324,304 and to U.S. Published Application No. 2010/0160954, which are incorporated herein by reference.

Figure 3:
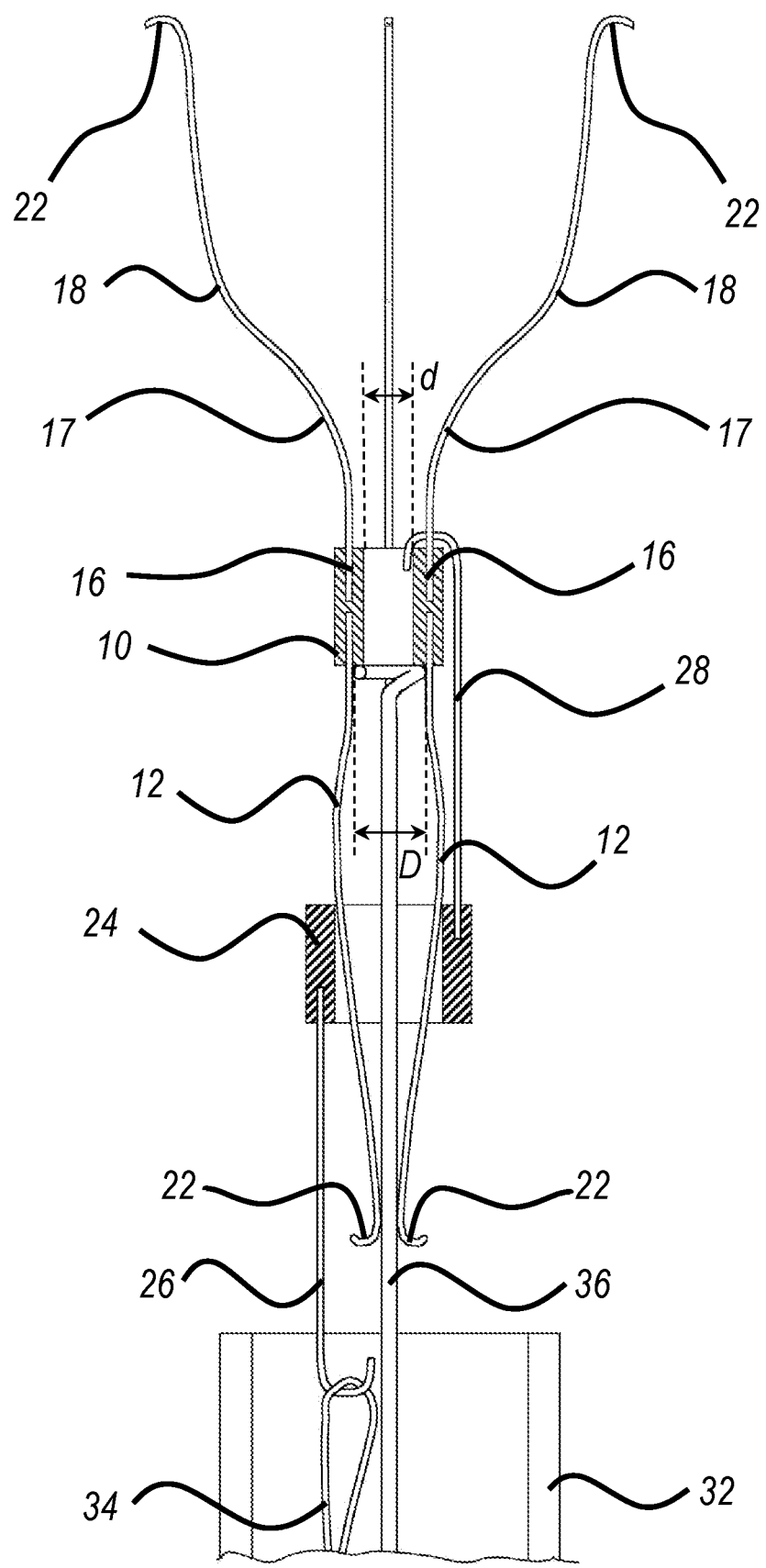
FIG. 3 is a cross-sectional view of the vena cava filter of FIG. 2 in a collapsed configuration during femoral removal.

Now making reference to FIG. 3, the movable hub 24 allows a physician to approach the deployed filter 20 from the femoral or jugular side and collapse the struts 12 or 14, respectively, such that the filter 20 can be captured within a recovery sheath 32 and retrieved from the patient's body.

Due to the symmetrical structure of the filter 20, the following description of a femoral removal by collapsing the femoral struts 12 is applicable in analogy to a jugular removal by collapsing the jugular struts 14. A snare 34 located at the distal end of a flexible rod (not shown) can be inserted within the lumen of the recovery sheath 32 and may be utilized to engage the femoral hook 26 and displace the movable hub 24 along the struts 12. During this step, the fixed hub 10 is not intended to move. To ensure that the fixed hub 10 remains at its axial location while the movable hub 24 is pulled along the struts 12, a push tool 36 may be used to hold the fixed hub 10 in place. The push tool 36 may be inserted through the recovery sheath 32 and be placed proximate the fixed hub 10 before the snare 34 engages the femoral hook 26 or after the snare 34 engages the femoral hook 26.

Where, as in the shown embodiment, the fixed hub 10 has an axial lumen, the push tool has a tip 38 with a radial diameter D that exceeds the diameter d of the lumen of the fixed hub 10, but smaller than the distance of opposing struts 12 from each other adjacent the fixed hub 10. For embodiments in which the fixed hub 10 has a solid tubular body, any push wire may be used to retain the fixed hub 10 in its axial position because a smaller abutment diameter is also suited for retaining the fixed hub 10 where the tubular body of the fixed hub 10 is solid.

The displacement of the movable hub 24 toward the hooks 22 forces the struts 12 to radially collapse toward the longitudinal axis X of the filter 20. The radially inward movement of the struts 12 disengages the anchoring hooks 22 from the vessel wall. The axial movement of the movable hub 24 along the struts 12 is limited by the axial length of the jugular hook 28. The jugular hook 28 is bent radially inward so that its free end abuts the fixed hub 10 once the jugular hook 28 has moved by a distance corresponding to the distance between its end and the fixed hub 10 in the expanded configuration shown in FIG. 2. Notably, the movable hub does not need to travel all the way to the anchoring hooks 22. It is sufficient that the movable hub travels past the first curved portion 17 of the struts 12 (shown in FIG. 2). The first curved portion 17 then provides that the struts 12 approach the longitudinal axis X without a further axial movement of the movable hub 24.

At this stage of the removal process, the push tool 36 is not needed any more. Thus, the push tool 36 may be removed separately, or it may be moved in the proximal direction along with the filter 20.

Once the struts 12 adjoining the recovery sheath 32 have been collapsed, the filter 20 can either be pulled proximally into the recovery sheath 32, or the recovery sheath 32 can be advanced distally to capture the filter 20 within the lumen of the recovery sheath 32. When the recovery sheath 32 passes the first curved portion 17 of the jugular struts 14, the sheath 32 abuts the jugular struts 14 and radially collapses the jugular struts 14 toward the central longitudinal axis X. The sheath 32 then accommodates the jugular struts 14 upon a further relative axial movement between the sheath 32 and the filter 20 until the entire filter 20 is surrounded by the recovery sheath 32.

As described above, the femoral hook 26 and the jugular hook 28 have a dual function. Each of them operates as a coupling member for the removal of the filter 20 in one direction and as a retainer for removal of the filter 20 in the other direction. It is within the scope of the present invention to implement coupling members other than hooks. Also, the coupling members may not have the dual function. The retaining function may be attained by different elements. For example, retaining elements include but are not limited to beads on the struts or an axially extending hook fastened on the fixed hub 10 on one or both of the axial sides of the fixed hub 10, where the respective hook is bent outward to catch the movable hub 24 when the movable hub reaches its intended travel distance from the fixed hub 10.

Figure 4:
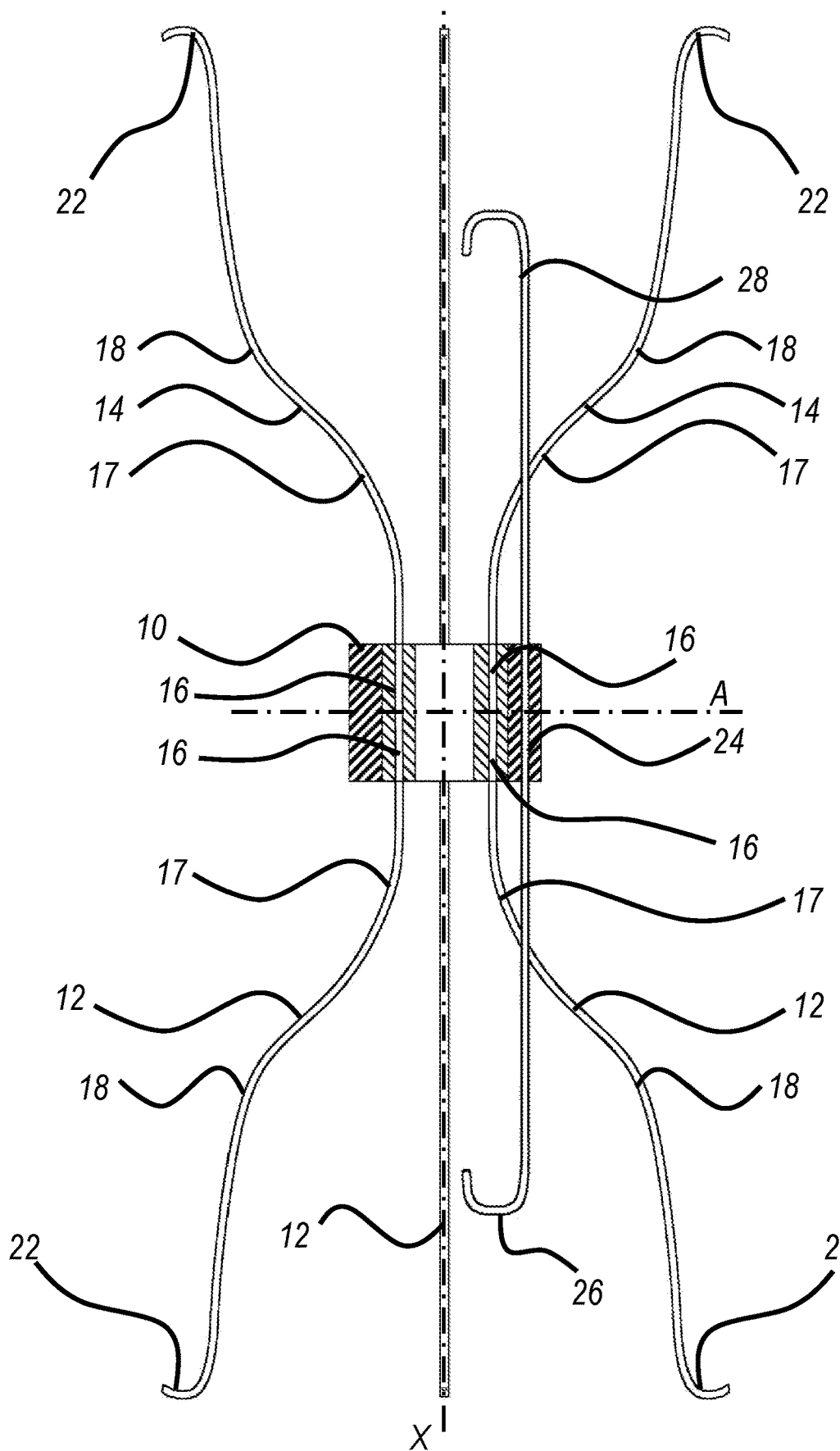
FIG. 4 shows an alternative embodiment of the vena cava filter of the present invention.

FIG. 4 shows a further embodiment of the filter 20. In the shown embodiment, each of the femoral struts 12 is unitarily formed with one of the jugular struts 14 so that the fixed ends 16 of a unitarily formed pair of femoral strut 12 and jugular strut 14 are connected inside the fixed hub 10. In a similar manner, the femoral hook 26 and the jugular hook 28 are formed in one piece axially extending through the fixed hub 10. Thus, the embodiment of the filter 20 shown in FIG. 4 comprises two generally identical adjoining halves on both axial sides of the radial plane A. The halves are arranged in mirror symmetry with respect to the virtual radial plane A.

As one skilled in the art having the benefit of this disclosure would appreciate, different materials, joining methods, and configurations may be implemented in manufacturing the filter.

While the present invention has been described in terms of preferred embodiments, it will be understood, of course, that the invention is not limited thereto since modifications may be made to those skilled in the art, particularly in light of the foregoing teachings.

What is claimed:

1. A method of removing an intravascular filter assembly from a body vessel, the filter assembly having a fixed hub defining a tubular body; a plurality of first struts extending from a first axial side of the fixed hub, the first struts having an expanded configuration when the filter is in an expanded state and a collapsed configuration when the filter is in a first collapsed state; a plurality of second struts extending from a second axial side of the fixed hub opposite the first axial side of the fixed hub, the second struts having an expanded configuration when the filter is in the expanded state and a collapsed configuration when the filter is in a second collapsed state; an axially movable hub having a first position radially surrounding at least an axial portion of the tubular body, a second position axially spaced apart from the fixed hub along the first struts, and a third position axially spaced apart from the fixed hub along the second struts, the first struts being in the collapsed configuration when the movable hub is in the second position, and the second struts being in the collapsed configuration when the movable hub is in the third position; a first coupling member extending from a first axial side of the movable hub, the first axial side of the movable hub coinciding with the first axial side of the fixed hub; and a second coupling member extending from a second axial side of the movable hub opposite the first axial side of the movable hub; the method comprising the steps of:

inserting a recovery sheath with a lumen into the body vessel from the first axial side;

placing a recovery tool within the lumen of the recovery sheath and moving it distally toward the filter assembly;

engaging the first coupling member with the recovery tool;

placing a push tool within the lumen of the recovery sheath and moving it distally toward the filter assembly;

abutting and retaining the fixed hub at a fixed location;

pulling the movable hub off the tubular portion along the first struts until the movable hub is in the second position and the first struts are in the collapsed configuration;

proximally removing the push tool;

causing a relative movement between the filter assembly and the recovery sheath in a direction that causes the filter assembly to enter the lumen of the recovery sheath;

collapsing the second struts with the recovery sheath by a further relative movement between the filter assembly and the recovery sheath;

continuing the relative movement between the filter assembly and the recovery sheath until the entire filter assembly is surrounded by the recovery sheath; and proximally removing the recovery sheath including the filter assembly.

2. The method of claim 1, wherein the push tool and the recovery sheath are removed simultaneously.

3. The method of claim 1, wherein the filter assembly further includes a retainer limiting a movement of the movable hub along the first struts and thereby defining the second position of the movable hub, wherein the movable hub is moved relative to the fixed hub until the retainer limits the movement.

4. The method of claim 3, wherein the retainer is a hook limiting the movement by abutting the fixed hub.

* * * * *